(12) United States Patent
Zhao et al.

(10) Patent No.: US 12,140,581 B2
(45) Date of Patent: Nov. 12, 2024

(54) MARINE TRANSPORTATION PLATFORM GUARANTEE-ORIENTED ANALYSIS AND PREDICTION METHOD FOR THREE-DIMENSIONAL TEMPERATURE AND SALINITY FIELD

(71) Applicant: Harbin Engineering University, Harbin (CN)

(72) Inventors: Yuxin Zhao, Harbin (CN); Rixu Hao, Harbin (CN); Jiaxun Li, Harbin (CN); Chang Liu, Harbin (CN); Qiuyang Zhang, Harbin (CN); Dequan Yang, Harbin (CN); Shuo Yang, Harbin (CN); Yanlong Liu, Harbin (CN); Hengde Zhao, Harbin (CN); Ting Zhao, Harbin (CN)

(73) Assignee: Harbin Engineering University, Harbin (CN)

( * ) Notice: Subject to any disclaimer, the term of this patent is extended or adjusted under 35 U.S.C. 154(b) by 289 days.

(21) Appl. No.: 17/847,496

(22) Filed: Jun. 23, 2022

(65) Prior Publication Data

US 2022/0326211 A1 Oct. 13, 2022

Related U.S. Application Data

(63) Continuation of application No. PCT/CN2022/080360, filed on Mar. 11, 2022.

(30) Foreign Application Priority Data

Mar. 15, 2021 (CN) .......................... 202110277125.9

(51) Int. Cl.
*G01N 33/18* (2006.01)
*G01C 13/00* (2006.01)

(52) U.S. Cl.
CPC ......... *G01N 33/1886* (2013.01); *G01C 13/00* (2013.01)

(58) Field of Classification Search
CPC .... G01N 33/1886; G01C 13/00; G06F 30/20; G06F 17/16; G06F 2111/10; G06F 30/23; G01P 1/00; Y02A 90/10
See application file for complete search history.

(56) References Cited

U.S. PATENT DOCUMENTS

2005/0265789 A1 12/2005 Sabri et al.

FOREIGN PATENT DOCUMENTS

| CN | 102004861 A | 4/2011 |
|---|---|---|
| CN | 103886180 A | 6/2014 |

(Continued)

*Primary Examiner* — Lisa M Caputo
*Assistant Examiner* — Cynthia L Davis
(74) *Attorney, Agent, or Firm* — IPRO, PLLC; Na Xu

(57) ABSTRACT

A method for a three-dimensional temperature and salinity field, including: based on multi-source marine environmental data, analyzing the spatiotemporal distribution characteristics of marine dynamic environmental elements, and studying the characteristics of the temperature-salinity relation; on the basis of analysis of the spatiotemporal characteristics and study of the characteristics of the temperature-salinity relation, establishing a statistical prediction model of marine environmental dynamic elements by a spatiotemporal empirical orthogonal function method; based on the observation data of temperature and salinity obtained by the marine transportation platform, correcting a marine environment forecast field around the marine transportation platform by using a realtime analysis technology of a marine environment field; and adjusting the salinity using a temperature-salinity relation curve after the temperature and salinity are forecasted.

2 Claims, 3 Drawing Sheets

(56) References Cited

FOREIGN PATENT DOCUMENTS

| CN | 111815041 | A | * | 10/2020 |
| CN | 112307410 | A | * | 2/2021 |
| CN | 113051795 | A | | 6/2021 |
| JP | 2004085394 | A | * | 3/2004 |
| JP | 2015135574 | A | | 7/2015 |

* cited by examiner

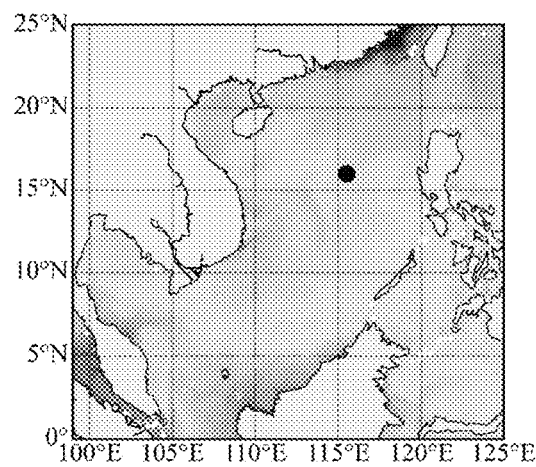 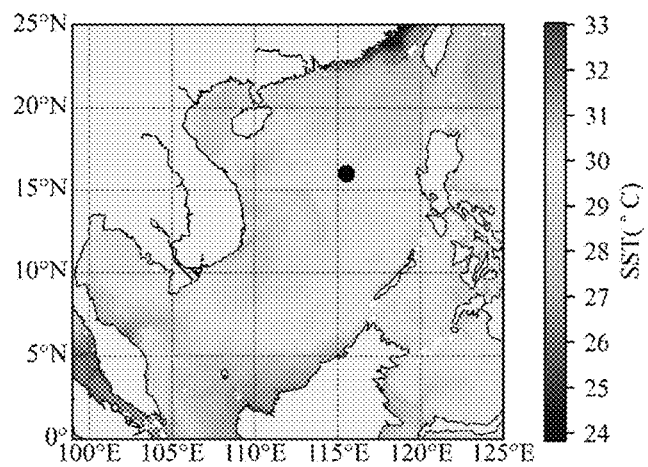
FIG. 4A                    FIG. 4B

MARINE TRANSPORTATION PLATFORM GUARANTEE-ORIENTED ANALYSIS AND PREDICTION METHOD FOR THREE-DIMENSIONAL TEMPERATURE AND SALINITY FIELD

TECHNICAL FIELD

The disclosure relates to a marine environment guarantee technology for marine transportation platform, and particularly designs a marine transportation platform guarantee-oriented analysis and prediction method for a three-dimensional temperature and salinity field based on a Spatiotemporal Empirical Orthogonal Function (STEOF) and Three-Dimensional Variational Assimilation (3D-VAR). The method of the disclosure is mainly applied to medium-to long-term analysis and prediction of marine dynamic environmental elements of marine transportation platforms such as ships, unmanned underwater/surface vehicles, and offshore engineering platforms during sailing, to solve the problem of large-area and long-term autonomous guarantee of the marine environment after failure of a numerical prediction product of the marine transportation platform.

BACKGROUND

The marine environment is a general term for environmental conditions including the marine atmospheric environment, ocean-atmosphere environment of boundary layer, the underwater hydrological environment and the seabed environment. Marine environmental guarantee is a general term for a series of professional activities that comprehensively use marine science and related science and technology to ensure safe, smooth and effective implementation of marine activities, by grasping the background characteristics, real-time status and evolution characteristics of the marine environment, diagnosing and predicting the rule of variation of the marine environment and future development trends, evaluating the impact of the marine environment, and proposing measures and suggestions to avoid or utilize marine environmental phenomena.

Marine environmental guarantee is a business for guaranteeing national coastal defense security, maintaining public social order and stability, providing reference information for the government to make decisions on the protection, development and utilization of the marine environment, and improving the efficiency of marine operations and the safety of people and property of marine-related departments, and also plays an important role in coastal defense development, economic construction, social stability, public health, marine environmental protection, and development and utilization of marine resources of country.

In the marine environment guarantee technology system, information acquisition, analysis and prediction, and the guarantee application technology are the most important components. From the perspective of the attribute and functional role of the marine environmental guarantee technology, information acquisition is the foundation, analysis and prediction are the core, and guarantee application is the link. As the core component of the marine environmental guarantee technology system, the analysis and prediction play an important role in the accuracy and real-time performance of prediction results for marine environmental guarantee.

The analysis and prediction of the maritime field mainly include two models: numerical prediction and statistical prediction. Although numerical prediction is the main means for marine environmental analysis and prediction at the present stage, it has shortcomings such as large computational load, imprecise initial conditions, and timeliness restrictions. Therefore, there is an urgent need for a prediction method that is less in computation and not restricted by timeliness than numerical prediction model to achieve rapid and accurate prediction of marine dynamic environmental elements.

The statistical prediction method is one of the important means in the analysis and prediction of the maritime field. When the sample data is large enough, the statistical prediction method can establish a data-driven prediction model without considering the physical laws of a research object. Therefore, the statistical prediction method does not have problems such as physical limit restrictions similar to the numerical prediction method. At present, the research on numerical prediction by major institutions around the world has become mature, but the traditional numerical prediction method cannot be used for extended period and medium-to long-term prediction, and a statistical prediction method needs to be considered. Therefore, the research on marine statistical analysis and prediction methods is necessary, and also plays an extremely important role in accurate prediction of the marine environment and timely grasp of marine information.

The disclosure aims at the requirements of marine environment guarantee for marine transportation platforms such as ships, unmanned underwater/surface vehicles, and offshore engineering, and develops a marine transportation platform guarantee-oriented analysis and prediction method for a three-dimensional temperature and salinity field based on a spatiotemporal empirical orthogonal function and three-dimensional variational assimilation, to improve the ability to analyze and forecast marine dynamic environmental elements, thereby solving the problem of large-area and long-term autonomous guarantee of the marine environment after failure of a numerical prediction product of the marine transportation platform.

SUMMARY

The objective of the disclosure is to meet the requirements of marine environment guarantee for marine transportation platforms such as ships, unmanned underwater/surface vehicles, and offshore engineering, and provides a small, fast and effective marine transportation platform guarantee-oriented analysis and prediction method for a three-dimensional temperature and salinity field. The method can effectively make up for the shortcoming of the traditional numerical prediction method that the period of prediction validity of marine dynamic environmental elements is short due to meteorologically driven timeliness restrictions, and the prediction process of the method does not require a high-performance computing platform and occupies less computing resource. The analysis and prediction method of the three-dimensional temperature and salinity field of the disclosure can be used for making a three-month valid statistical analysis and forecast on the marine dynamic environmental elements, provides technical support for solving the technical problem of large-area and long-term autonomous guarantee of the marine environment after failure of a marine numerical prediction product, and is of great scientific significance and application value.

The objective of the disclosure is achieved as follows:

Disclosed is a marine transportation platform guarantee-oriented analysis and prediction method for a three-dimensional temperature and salinity field based on a spatiotemporal empirical orthogonal function and three-dimensional variational assimilation, including:

(1) based on multi-source marine environmental data, analyzing the spatiotemporal distribution characteristics of marine dynamic environmental elements, and studying the characteristics of the temperature-salinity relation;

(2) on the basis of analysis of the spatiotemporal characteristics and study of the characteristics of the temperature-salinity relation, establishing a statistical prediction model of marine environmental dynamic elements by a spatiotemporal empirical orthogonal function method;

(3) based on the observation data of sea surface temperature and salinity obtained by the marine transportation platform, correcting a marine environment forecast field around the marine transportation platform by using a real-time analysis technology of a marine environment field to improve the prediction accuracy of the marine environment around the marine transportation platform;

(4) to maintain the consistency of a sea surface temperature and salinity structure in the forecast results, adjusting the salinity using a temperature-salinity relation curve after the temperature and salinity are forecasted, so as to keep the temperature-salinity relation as close as possible to its climatic characteristics.

Based on multi-source marine environmental data such as satellite remote sensing, historical statistics, and reanalysis, the disclosure uses a statistical analysis method to establish a marine transportation platform-oriented medium-to long-term forecast model for a three-dimensional temperature and salinity field, and uses historical statistical data stored in the marine transportation platform database, measured environmental data, forecast data and other information as input to realize correction of medium-to long-term forecast of the three-dimensional temperature and salinity field in a target sea area. The disclosure overcomes the timeliness restriction problem of the traditional marine numerical prediction method, greatly improves the ability to predict marine dynamic environmental elements in a medium-to long-term, and provides technical support to solve the technical problem of large-area and long-term autonomous guarantee of the marine environment of marine transportation platform after failure of a marine numerical prediction product.

A marine transportation platform guarantee-oriented analysis and prediction method for a three-dimensional temperature and salinity field, including the following steps:

Step 1: carrying out statistical analysis for marine dynamic environmental elements based on multi-source marine environmental data, mainly including analysis of the spatiotemporal distribution characteristics of the marine dynamic environmental elements and study of the characteristics of the temperature-salinity relation of the marine dynamic environmental elements.

Using multi-source marine environmental data such as a global high-resolution marine reanalysis product, a marine environment numerical prediction product, and satellite remote sensing, statistical analysis of various data under specific spatiotemporal conditions required for marine platform guarantee is carried out.

1) Analysis of the Spatiotemporal Distribution Characteristics of the Marine Dynamic Environmental Elements The analysis of the spatiotemporal distribution characteristics of the marine dynamic environmental elements mainly includes preprocessing analysis of previous observation and reanalysis data, by a variety of spatiotemporal analysis methods such as data distribution test and variance analysis. A selected element is analyzed by an Empirical Orthogonal Function (EOF) analytical method for the main spatiotemporal distribution patterns. The basic idea of the EOF is to decompose a spatiotemporal variation field into a time-independent spatial function and a time-dependent temporal function which are relatively independent. The result of the EOF shows that an element to be analyzed is determined by several main spatial distribution patterns, and each distribution pattern has the corresponding temporal variation respectively, resulting in different intensities of each spatial pattern at different time.

For the analysis of extreme events, the regression period of each sea area and the element value under a certain regression period of a certain element when reaching a certain intensity are computed by an extreme value statistical method and a generalized extreme value statistical method. The purpose of the study and analysis is to provide basic background information on the ocean and provide reference for navigation planning over the season.

2) Study of the Characteristics of the Temperature-Salinity Relation

The study of the characteristics of the temperature-salinity relation is mainly based on statistical analysis of the above-mentioned spatiotemporal distribution characteristics of marine elements, and a reanalysis data product and the historical observation profile data of temperature and salinity are used for analyzing the temperature and salinity correlation statistics at different time scales in each sea area. The characteristic curves of temperature and salinity at different time scales in each sea area are determined to provide a data base for salinity correction.

Step 2: on the basis of analysis of the spatiotemporal characteristics and study of the characteristics of the temperature-salinity relation, establishing a statistical prediction model of marine environmental dynamic elements by a spatiotemporal empirical orthogonal function method. Based on a high-resolution marine reanalysis product for a sea area to be analyzed and forecasted, a spatiotemporal sample matrix of daily marine dynamic environmental elements over the years in a space to be analyzed is constructed. The method for constructing the spatiotemporal sample matrix is as follows: for a certain marine dynamic environmental element, the corresponding spatiotemporal sample matrix X of the daily marine dynamic environmental element over the years in the space to be analyzed is:

$$X = \begin{bmatrix} x_{1,1}^1 & \cdots & x_{n,1}^1 & \cdots & x_{N,1}^1 & \cdots & x_{1,t}^1 & \cdots & x_{n,t}^1 & \cdots & x_{N,t}^1 & \cdots & x_{1,T}^1 & \cdots & x_{n,T}^1 & \cdots & x_{N,T}^1 \\ \vdots & \ddots & \vdots & \ddots & \vdots & \ddots & \vdots & \ddots & \vdots & \ddots & \vdots & \ddots & \vdots & \ddots & \vdots & \ddots & \vdots \\ x_{1,1}^m & \cdots & x_{n,1}^m & \cdots & x_{N,1}^m & \cdots & x_{1,t}^m & \cdots & x_{n,t}^m & \cdots & x_{N,t}^m & \cdots & x_{1,T}^m & \cdots & x_{n,T}^m & \cdots & x_{N,T}^m \\ \vdots & \ddots & \vdots & \ddots & \vdots & \ddots & \vdots & \ddots & \vdots & \ddots & \vdots & \ddots & \vdots & \ddots & \vdots & \ddots & \vdots \\ x_{1,1}^M & \cdots & x_{n,1}^M & \cdots & x_{N,1}^M & \cdots & x_{1,t}^M & \cdots & x_{n,t}^M & \cdots & x_{N,t}^M & \cdots & x_{1,T}^M & \cdots & x_{n,T}^M & \cdots & x_{N,T}^M \end{bmatrix} \quad (1)$$

where X represents the spatiotemporal sample matrix of daily marine dynamic environment elements over the years, n represents the number of spatial grid points, t represents the number of time series, and m represents the number of annual samples.

For any spatiotemporal sample matrix X, of which the matrix dimension is M×(N×T), singular value decomposition is performed for the spatiotemporal sample matrix X, the eigenvalues of the matrix and the eigenvector corresponding to each eigenvalue are obtained, the total proportion of each eigenvalue is computed in turn, and the eigenvalues and eigenvectors are arranged in order. The eigenvectors at this time are the time series of a spatial mode, which contain both spatial information and temporal information, and such an eigenvector is called a spatiotemporal base.

Since the eigenvalues and eigenvectors of a covariance matrix of the spatiotemporal sample matrix X are usually solved by the Jacobi iterative method, when the rank of the matrix is large, the Jacobi iterative method requires a large amount of computation. The number N×T of the spatiotemporal grid points is much larger than the number of period M, so it is necessary to perform spatiotemporal transformation to reduce the amount of computation. Obviously, $C = X \cdot X^T$ and $C^* = X^T \cdot X$ have the same non-zero eigenvalues, but different eigenvectors. Therefore, after the eigenvectors of the C* matrix are obtained through matrix transformation, the eigenvectors of the C matrix can be computed, and the product of $\widetilde{X}_i$ and its transposed matrix can be expressed as follows:

$$C^* = \frac{1}{n} X^T \times X \quad (2)$$

The eigenvector $V_{M \times M}$ is:

$$C^* \times V^* = V^* \times \Lambda \quad (3)$$

where $\Lambda$ is a diagonal square matrix corresponding to the eigenvalues, as follows:

$$\Lambda = \begin{bmatrix} \lambda_1 & \cdots & 0 & \cdots & 0 \\ \vdots & \ddots & \vdots & & \vdots \\ 0 & \cdots & \lambda_m & \cdots & 0 \\ \vdots & & \vdots & \ddots & \vdots \\ 0 & \cdots & 0 & \cdots & \lambda_M \end{bmatrix} \quad (4)$$

where $\lambda_1 > \ldots > \lambda_m > \ldots > \lambda_M$.
Any eigenvector $V_m$ is as follows:

$$V_m = \frac{1}{\sqrt{\lambda_m}} \widetilde{x}_i \times V^* \quad (5)$$

where each column of eigenvector values has one non-zero eigenvalue in one-to-one correspondence therewith, and such an operation is called spatiotemporal empirical orthogonal decomposition. The eigenvectors obtained by the spatiotemporal empirical orthogonal decomposition are the time series of a spatial mode, which contain both spatial and temporal information, which we call a spatiotemporal base. Each spatiotemporal base represents the evolution of spatial patterns over time. Therefore, the spatiotemporal empirical orthogonal decomposition method extracts the main characteristics of the temporal variation of the spatial patterns based on historical data.

The corresponding principal components can be obtained by projecting spatiotemporal modes onto the matrix $\widetilde{X}_i$, as follows:

$$PC_{M \times (N \times T)} = V^T_{M \times (N \times T)} \times \widetilde{X}_{M \times (N \times T)} \quad (6)$$

The principal components are the spatiotemporal coefficients corresponding to each spatiotemporal eigenvector. The spatiotemporal coefficients $PC_{M \times (N \times T)}$ is a M×(N×T) dimensional matrix, each row of data in $PC_{M \times (N \times T)}$ is the space-time coefficient corresponding to each space-time mode, the space-time coefficient of the first space-time mode corresponds to the first row of the spatiotemporal coefficient $PC_{M \times (N \times T)}$, and so on.

Using the proposed spatiotemporal empirical orthogonal function decomposition method, the prediction problem of marine dynamic environmental elements in an area to be analyzed can be transformed from a time extrapolation problem to a problem of finding similar processes from historical time series variations. A set of spatiotemporal bases is established using the decomposition results of multiple spatiotemporal series, and spatiotemporal series are predicted by spatiotemporal observations and the spatiotemporal bases.

The spatiotemporal observation value $O_i$ is as follows:

$$O_i = [o_{1,t-l} \ldots o_{N,t-l} \ldots o_{1,t-l+i} \ldots o_{N,t-l+i} \ldots \\ o_{1,t} \ldots o_{N,t}]^T \quad (7)$$

where $O_i$ represents the spatiotemporal observation, t represents the prediction start time, n represents the number of spatial grid points, and l represents the number of observations.

The spatiotemporal base $H_i$ is divided into two parts: one is a fitting spatiotemporal base $H_{i,f}$ with the same period as the spatiotemporal observation, and the other is a predicted spatiotemporal base $H_{i,p}$.

$$H_i = \begin{bmatrix} h_{1,t-l}^1 & \cdots & h_{N,t-l}^1 & \cdots & h_{1,t-l+j}^1 & \cdots & h_{N,t-l+j}^1 & \cdots & h_{1,t+p}^1 & \cdots & h_{N,t+p}^1 \\ \vdots & \ddots & \vdots & \ddots & \vdots & \ddots & \vdots & \ddots & \vdots & \ddots & \vdots \\ h_{1,t-l}^m & \cdots & h_{N,t-l}^m & \cdots & h_{1,t-l+j}^m & \cdots & h_{N,t-l+j}^m & \cdots & h_{1,t+p}^m & \cdots & h_{N,t+p}^m \\ \vdots & \ddots & \vdots & \ddots & \vdots & \ddots & \vdots & \ddots & \vdots & \ddots & \vdots \\ h_{1,t-l}^M & \cdots & h_{N,t-l}^M & \cdots & h_{1,t-l+j}^M & \cdots & h_{N,t-l+j}^M & \cdots & h_{1,t+p}^M & \cdots & h_{N,t+p}^M \end{bmatrix}^T \quad (8)$$

For the spatiotemporal base decomposed for a historical long time, a spatial time series matrix can be divided into two parts: a fitting spatial time series matrix $H_{i,f}$ with the same time as the observation data and a forecasted spatial time series matrix $H_{i,p}$ with the same time as the prediction.

$$H_{i,f} = \begin{bmatrix} h^1_{1,t-l} & \cdots & h^1_{N,t-l} & \cdots & h^1_{1,t-l+j} & \cdots & h^1_{N,t-l+j} & \cdots & h^1_{1,t} & \cdots & h^1_{N,t} \\ \vdots & \ddots & \vdots & \ddots & \vdots & \ddots & \vdots & \ddots & \vdots & \ddots & \vdots \\ h^m_{1,t-l} & \cdots & h^m_{N,t-l} & \cdots & h^m_{1,t-l+j} & \cdots & h^m_{N,t-l+j} & \cdots & h^m_{1,t} & \cdots & h^m_{N,t} \\ \vdots & \ddots & \vdots & \ddots & \vdots & \ddots & \vdots & \ddots & \vdots & \ddots & \vdots \\ h^M_{1,t-l} & \cdots & h^M_{N,t-l} & \cdots & h^M_{1,t-l+j} & \cdots & h^M_{N,t-l+j} & \cdots & h^M_{1,t} & \cdots & h^M_{N,t} \end{bmatrix}^T \quad (9)$$

$$H_{i,p} = \begin{bmatrix} h^1_{1,t+1} & \cdots & h^1_{N,t+1} & \cdots & h^1_{1,t+j} & \cdots & h^1_{N,t+j} & \cdots & h^1_{1,t+p} & \cdots & h^1_{N,t+p} \\ \vdots & \ddots & \vdots & \ddots & \vdots & \ddots & \vdots & \ddots & \vdots & \ddots & \vdots \\ h^m_{1,t+1} & \cdots & h^m_{N,t+1} & \cdots & h^m_{1,t+j} & \cdots & h^m_{N,t+j} & \cdots & h^m_{1,t+p} & \cdots & h^m_{N,t+p} \\ \vdots & \ddots & \vdots & \ddots & \vdots & \ddots & \vdots & \ddots & \vdots & \ddots & \vdots \\ h^M_{1,t+1} & \cdots & h^M_{N,t+1} & \cdots & h^M_{1,t+j} & \cdots & h^M_{N,t+j} & \cdots & h^M_{1,t+p} & \cdots & h^M_{N,t+p} \end{bmatrix}^T \quad (10)$$

where t represents the start time of prediction, N represents the number of spatial grid points, l represents the number of observations, p represents the number of timesteps of prediction, and M represents the number of spatiotemporal bases.

The eigenvectors of the spatiotemporal matrix are orthogonal to each other, that is, the spatiotemporal base is linearly independent. For linearly independent base functions, Least Square Estimation (LSE) is the optimal fitting method. The fitting coefficients and fitting spatiotemporal bases of the spatiotemporal observations are solved by the LSE method. The fitting coefficients are projections of spatiotemporal observations on each spatiotemporal base, describing the similarity between a set of observations and the spatiotemporal base:

$$O_i = H_{i,f} S_i \quad (11)$$

where S represents the fitting coefficients, as follows:

$$S_i = [S_{i,1} \ldots S_{i,m} \ldots S_{i,M}] \quad (12)$$

where m represents the m-th mode.

Each spatiotemporal base can be regarded as a description of the rule of variation of a spatiotemporal series. Therefore, when the rule of the spatiotemporal series in the fitting stage can be described by the spatiotemporal base, the variation in the spatiotemporal series in the prediction stage also conforms to the same rule. From this, future values of the spatiotemporal series are predicted by reconstructing the fitting coefficients and predicting the spatiotemporal base. Therefore, the spatiotemporal series is predicted using a spatiotemporal empirical orthogonal function prediction model which combines the spatiotemporal empirical orthogonal decomposition method and the least square method, and the prediction model is as follows:

$$Y_i = H_{i,p} \cdot S_i = [y_{i,1,t+1} \; \cdots \; y_{i,N,t+1} \; \cdots \; y_{i,1,t+j} \; \cdots \; y_{i,N,t+j} \; \cdots \; y_{i,1,t+p} \; \cdots \; y_{i,N,t+p}]^T \quad (13)$$

where Y represents the spatiotemporal prediction result, N represents the number of spatial grid points, t represents the start time of prediction, and p represents the number of timesteps of prediction.

Step 3: based on the observation data of sea surface temperature and salinity obtained by a marine transportation platform, correcting a marine environment forecast field around the marine transportation platform by using a real-time analysis technology of a marine environment field to improve the prediction accuracy of the marine environment around the marine transportation platform.

A real-time analysis technology of the marine environment field around the marine transportation platform aims to establish a modular data assimilation system installed on the marine transportation platform. Compared with a shore-based modular data assimilation system, the real-time analysis system of the marine environment of the marine transportation platform is smaller and more flexible in data processing and implementation methods, and has a function of analyzing and predicting the marine environment field below the water surface. Moreover, due to the limited means of obtaining observation data and less real-time observation data during the navigation of the marine transportation platform, the real-time analysis technology of the marine environment of the marine transportation platform has a particularity. To realize the real-time analysis of the marine environment of the marine transportation platform, it is necessary to solve the following technical problems: construction of a marine environment background field, inversion of a three-dimensional temperature and salinity field, assimilation of the observation data of the marine transportation platform, and the like.

1) Construction of the Marine Environment Background Field

For the construction of the marine environment background field, combined with the characteristics of the marine transportation platform, the following three methods are proposed to obtain the marine environment background field according to available data:

a) When a shore-based marine numerical prediction product transmitted by a shore-based security department is available, the shore-based marine numerical prediction product is loaded into a marine environment database of the marine transportation platform before sailing, and used as the background field. Using a multi-scale marine data assimilation method, real-time/quasi-real-time multi-source marine observation data of the marine transportation platform is assimilated to form a high-precision real-time analysis field of the marine environment around the marine transportation platform.

b) When a shore-based numerical prediction product is not available, real-time/quasi-real-time satellite remote sensing sea surface temperature and satellite altimeter data published on the Internet can be directly downloaded, and loaded into a marine environment data platform of the marine transportation platform before sailing, and then underwater temperature and salinity data is inverted based on a real-time analysis system of the marine transportation platform. The three-dimensional temperature and salinity field obtained by the inversion can be used as an initial field for inertial prediction, which can provide the background field for real-time analysis of the marine environment in a short time before sailing, and make a real-time analysis product of the marine environment field around an underwater vehicle.

c) When the marine transportation platform has been sailing for a long time (more than 15 days) and the shore-based prediction product loaded fails, based on a reanalysis or statistical prediction product, underwater temperature and salinity data is inverted based on the real-time analysis system of the marine transportation platform, and a real-time analysis product of the marine environment field around the underwater vehicle is made.

2) Inversion of the Three-Dimensional Temperature and Salinity Field

Three-dimensional temperature and salinity field inversion is a main method to obtain a marine environmental field by using satellite remote sensing data to invert a three-dimensional temperature and salinity field when a shore-based prediction product and a real-time reanalysis data product are not available. Before sailing, the downloaded satellite sea surface temperature and sea surface height anomaly data are used for inverting to obtain the three-dimensional temperature and salinity field, and based on this, statistical prediction or inertial prediction of temperature and salinity is performed to construct a real-time analysis background field. The main technical processes include: construction of a static temperature and salinity climate field, construction of a dynamic background field, the inversion of the three-dimensional temperature and salinity field, and the like.

a) Construction of a Static Temperature Climate Field

Taking a temperature climatic state analysis product (such as WOA01) as an initial guess field, historical temperature profile observation data that has undergone processing and quality control is assimilated by using an optimal interpolation data assimilation technology, and static temperature climate field products at different water depths and each horizontal grid point are formed.

The temperature observation data $T_{j,k}^o$ at a position j is formed by the optimal interpolation method into the climatological temperature data $T_{i,k}^c$ at each grid point position i, at the k-th layer in depth:

$$T_{i,k}^c = T_{i,k}^B + \sum_{j=1}^{N} w_{i,j}(T_{j,k}^o - T_{j,k}^B) \quad (14)$$

where $T_{i,k}^B$ is the climatic background field (such as WOA01).

The weight coefficient $w_{i,j}$ in the above equation is solved by the following equation:

$$C_i W_i = F_i \quad (15)$$

where $w_{i,j}$ (j=1, ..., N) is an element of matrix $W_i$, and $c_{m,n}$ is an element of matrix $C_i$, which is equal to the sum of error covariance $c_{m,n}^{fg}$ of the initial guess temperature and covariance $c_{m,n}^o$ of observation errors $r_m$ and $r_n$ at different observation positions.

b) Construction of a Static Salinity Climate Field

Using historical observation data of temperature and salinity profiles that has undergone strict quality control and fine processing, for different regions, grids and different time periods, an empirical regression model of inversion of salinity from temperature is established using a regression analysis method.

$$S_{i,k}(T) = \overline{S_{i,k}} + a_{i,k}^{S1}(T - \overline{T_{i,k}}) \quad (16)$$

where $$\overline{S_{i,k}} = \frac{\sum_{j=1}^{N^{TS}} b_{i,j} S_{j,k}^O}{\sum_{j=1}^{N^{TS}} b_{i,j}} \quad (17)$$

$$\overline{T_{i,k}} = \frac{\sum_{j=1}^{N^{TS}} b_{i,j} T_{j,k}^O}{\sum_{j=1}^{N^{TS}} b_{i,j}} \quad (18)$$

$$a_{i,k}^{S1} = \frac{\sum_{j=1}^{N^{TS}} b_{i,j}(S_{j,k}^O - \overline{S_{j,k}})(T_{j,k}^O - \overline{T_{j,k}})}{\sum_{j=1}^{N^{TS}} b_{i,j}(T_{j,k}^O - \overline{T_{j,k}})^2} \quad (19)$$

where $b_{i,j}$ is a local correlation function:

$$b_{i,j} = \exp\{-[(x_i - x_j)/L_x]^2 - [(y_i - y_j)/L_y]^2 - [(t_i - t_j)/L_t]^2\} \quad (20)$$

where x and y are the longitudinal and latitudinal positions respectively; t is time; $L_x$, $L_y$, and $L_t$ are length and time correlation scales respectively.

The static temperature climate field is substituted into the temperature-salinity correlation model established above to generate static salinity climate field products at different water depths and each horizontal grid point.

c) Inversion of a Temperature Profile from SST

On the basis of a lot of rigorous analysis of historical temperature observation data, an empirical regression model for the inversion of the temperature profile from SST is established:

$$T_{i,k}(SST) = \overline{T_{i,k}} + a_{i,k}^{T1}(sst - \overline{T_{i,1}}) \quad (21)$$

where $T_{i,k}$ (SST) is the temperature value at grid point i and depth k inverted from the sea surface temperature, $\overline{T_{i,k}}$ is the average temperature, SST is the sea surface temperature, and $a_{i,k}^{T1}$ is a regression coefficient.

d) Inversion of a Temperature Profile From SSH

On the basis of a lot of rigorous analysis of historical observation data of temperature and salinity, an empirical regression model for the inversion of the temperature profile from SSH is established:

$$T_{i,k}(h) = \overline{T_{i,k}} + a_{i,k}^{T2}(h - \overline{h_i}) \quad (22)$$

where $T_{i,k}$ (h) is the temperature value at grid point i and depth k inverted from sea surface height, $a_{i,k}^{T2}$ is a regression coefficient, and h and $\overline{h_i}$ are dynamic height anomaly (deviation) and its average value respectively.

The dynamic height anomaly (deviation) is computed by:

$$h = \int_0^H \frac{[v(T, S, p) - v(0, 35, p)]}{v(0, 35, p)} dz \quad (23)$$

where v is the specific volume of seawater, v(0,35,p) is the specific volume of seawater when the seawater temperature is 0° C. and the salinity is 35 psu, and H is the water depth.

In order to use as much temperature and salinity profile data as possible for regression analysis, it is necessary to use historical observation data of temperature and salinity profiles that has undergone strict quality control. For the observation data of temperature and salinity that does not reach the seabed depth, through repeated experiments, a temperature profile extension model is established based on an empirical orthogonal function analysis (EOF) method. The temperature observation data that does not reach the required depth is extended using the model to the seabed to obtain the entire temperature salinity profile. For the profile with missing salinity measurement, the salinity profile is obtained from the temperature profile by using the temperature-salinity relation model established above.

A complete temperature profile is obtained by superimposing a synthetic temperature profile $T_k^{syn}$ onto an observed profile with observation not reaching the seabed:

$$T_k = T_k^{syn} + [T_{k\,max}^o - T_{k\,max}^{syn}]\exp[-(z_k - z_{k\,max})/L_z] \quad (24)$$

where $L_z$ is a vertical correlation scale, $z_k > z_{k\,max}$.

The synthetic temperature profile $T_k^{syn}$ is computed by fitting the temperature profile observation that does not reach the seabed to the average temperature and superimposing the empirical orthogonal function $E_k$ corresponding to the maximum eigenvalue:

$$T_{j,k}^{syn} = \overline{T_{j,k}} + g_j e_k \quad (25)$$

where $g_j$ is the amplitude of the maximum orthogonal function, computed by:

$$g_j = \frac{\sum_{k=1}^{M_j} w_k [e_k(T_{j,k}^o - \overline{T_{j,k}})]}{\sum_{k=1}^{M_j} w_k} \quad (26)$$

where weight w is defined as $w_k = (z_k - z_{k-1})^{1/4}, k=2,\ldots,M_j$, $w_1 = w_2$.

e) Joint Inversion of a Temperature Profile From SST and SSH

On the basis of a lot of rigorous analysis of historical observation data of temperature and salinity, an empirical regression model for the inversion of the temperature profile from SST and SSH is established:

$$T_{i,k}(sst,h) = \overline{T_{i,k}} + a_{i,k}^{T3}(SST - \overline{T_{i,1}}) + a_{i,k}^{T4}(h - \overline{h_i}) + a_{i,k}^{T5}[(SST - \overline{T_{i,1}})(h - \overline{h_i}) - \overline{hSST_i}] \quad (27)$$

where $T_{i,k}$ (sst,h) is the temperature value at grid point i and depth k inverted by sea surface temperature and sea surface height anomalies (deviations), and $a_{i,k}^{T3}$, $a_{i,k}^{T4}$ and $a_{i,k}^{T5}$ are regression coefficients.

3) Assimilation of Observation Data of the Marine Transportation Platform

To improve the accuracy of real-time analysis as much as possible, the dynamic background field of the marine environment is further corrected by using the real-time observation data of temperature and salinity obtained by the marine transportation platform. The disclosure uses a multi-grid three-dimensional variational assimilation technology for correcting the background field. The method can quickly extract multi-scale information from an observation system from long wave to short wave in turn, occupies small memory, has high computing speed, and is very suitable for a computer carried on the marine transportation platform. In multigrid three-dimensional variational data assimilation, long-wave information can be analyzed using a coarse-grid objective functional, while short-wave information can be analyzed using a fine-grid objective functional. Therefore, the target functional in the multigrid three-dimensional variational data assimilation method is as follows:

$$J^{(n)} = \tfrac{1}{2}X^{(n)T}X^{(n)} + \tfrac{1}{2}(H^{(n)}X^{(n)} - Y^{(n)})^T O^{(n)-1}(H^{(n)}X^{(n)} - Y^{(n)}) \quad (28)$$

where $$\begin{cases} X = X^a - X^b \\ Y = Y^{obs} - HX^b \end{cases} \quad (29)$$

where n represents the n-th grid, n=1,2,3, ..., N, $X^b$ is a model background field (prediction field) vector, $X^a$ is an analysis field vector, $Y^{obs}$ is an observation field vector; O is an observation field error covariance matrix; H is a bilinear interpolation operator from the model grid to the observation point; X is a control variable, which represents the correction vector relative to the model background field vector, Y is the difference between the observation field and the model background field, and $$\begin{cases} Y^{(1)} = Y^{obs} - HX^b \\ Y^{(n)} = Y^{(n-1)} - H^{(n-1)}X^{(n-1)} (n=2, 3, \ldots, N) \end{cases} \quad (30)$$

where coarse grids correspond to long-wave modes, and fine grids correspond to short-wave modes. Since the wavelength or correlation scale is expressed by the thickness of a grid, the background field error covariance matrix degenerates into a simple identity matrix. The final analysis result can be expressed as:

$$X^a = X^b + X_L = X^b + \sum_{n=1}^{N} X^{(n)} \quad (31)$$

From coarse grids to fine grids, three-dimensional variational analysis is performed on the increment of the observation field relative to the background field in turn. In the process of each analysis, the analysis field obtained from the previous analysis on a coarser grid is substituted into the analysis of a next finer grid as a new background field. The increment of each analysis also refers to the increment relative to the new background field obtained by the previous coarser grid analysis. Finally, the analysis results of all grids are superimposed to obtain the final analysis result. In the above multigrid three-dimensional variational method, the vertical gradient of marine environmental elements is proposed to be introduced into the objective functional as a constraint condition, so as to improve the analysis ability of a spring layer.

Step 4: the influence of salinity variation on density is non-negligible, and making statistical prediction for temperature and salinity separately will cause the destruction of the thermodynamic structure of a marine state field, which leads to dynamic instability of the ocean. To maintain the consistency of a sea surface temperature and salinity structure, correcting the salinity after the temperature and salinity are forecasted.

At present, there are many salinity adjustment schemes in the world. The European Centre for Medium-Range Weather Forecasts (ECMWF) adjusts the salinity by changing the temperature and salinity profiles. The NCEP in the United States adjusts the temperature and salinity using the observation data of sea surface height and temperature by the three-dimensional variational method. Learning from the salinity adjustment scheme of the ECMWF, in the disclosure, after the temperature and salinity are statistically forecasted, the salinity is adjusted by using a temperature-salinity relation curve, and the temperature-salinity relation is kept as close as possible to its climatic characteristics.

The disclosure uses the aforementioned statistical results to analyze the climatic seasonal characteristics of the temperature-salinity relation in each sea area, and simultaneously analyze the influence of high-frequency fluctuations of temperature and salinity on the temperature-salinity relation, thereby determining the temperature-salinity relation curves and envelopes of characteristics thereof in different sea areas and different seasons. The salinity data of which the prediction results deviate from the temperature-salinity curve is corrected by the nudging method.

Compared with the prior art, the disclosure has the following beneficial effects:

Based on multi-source marine environmental data such as satellite remote sensing, historical statistics, and reanalysis, the disclosure uses a statistical analysis method to establish a marine transportation platform-oriented medium-to long-term forecast model for a three-dimensional temperature and salinity field of seawater, and uses historical statistical data stored in the marine transportation platform database, measured environmental data, forecast data and other information as input to realize correction of medium-to long-term forecast of the three-dimensional temperature and salinity field in a target sea area. The disclosure overcomes the timeliness restriction problem of the traditional marine numerical prediction method, greatly improves the ability to predict marine dynamic environmental elements in a medium-to long-term, and provides technical support to solve the technical problem of large-area and long-term autonomous guarantee of the marine environment of marine transportation platform after failure of a marine numerical prediction product.

BRIEF DESCRIPTION OF FIGURES

FIG. 4A-4B shows a comparison diagram of sea temperature analysis and prediction results with a period of validity of 90 days according to the disclosure.

FIG. 4A shows observation results of sea temperature forecast with a period of validity of 90 days according to the disclosure.

FIG. 4B shows analysis and prediction results of sea temperature forecast with a period of validity of 90 days according to the disclosure.

DETAILED DESCRIPTION

Figure 1:
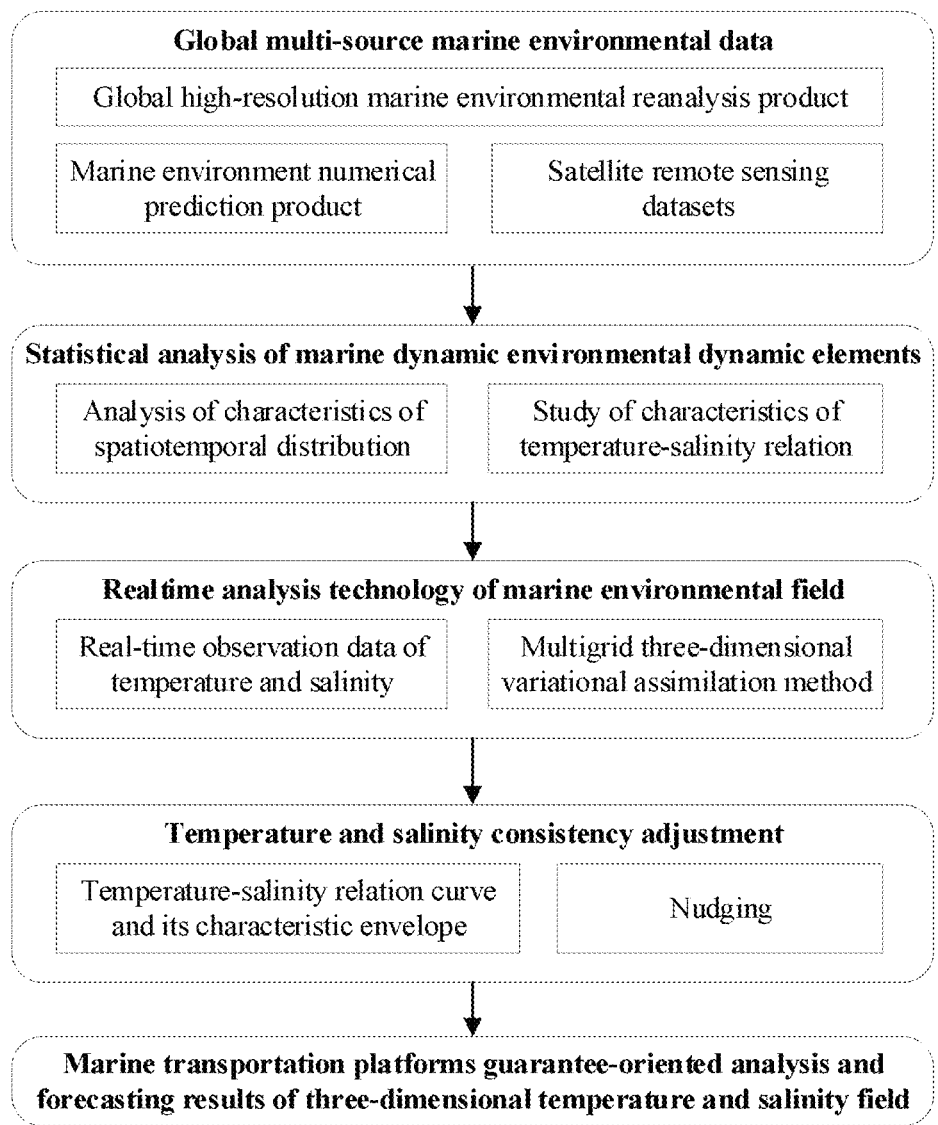
FIG. 1 shows a flow chart of the method of the disclosure.

The disclosure is further described in detail below with reference to the accompanying drawings and specific examples.

The disclosure uses the technical solutions as follows: a marine transportation platform guarantee-oriented analysis and prediction method for a three-dimensional temperature and salinity field, including the following steps:

Step 1: statistical analysis is carried out for marine dynamic environmental elements based on multi-source marine environmental data, mainly including analysis of the spatiotemporal distribution characteristics of the marine dynamic environmental elements and study of the characteristics of the temperature-salinity relation of the marine dynamic environmental elements.

Using multi-source marine environmental data such as a global high-resolution marine reanalysis product, a marine environment numerical prediction product, and satellite remote sensing, statistical analysis of various data under specific spatiotemporal conditions required for marine platform guarantee is carried out, mainly including analysis of the spatiotemporal distribution characteristics of the marine dynamic environmental elements and study of the characteristics of the temperature-salinity relation of the marine dynamic environmental elements.

1) Analysis of the Spatiotemporal Distribution Characteristics of the Marine Dynamic Environmental Elements The analysis of the spatiotemporal distribution characteristics of the marine dynamic environmental elements mainly includes preprocessing analysis of previous observation and reanalysis data, by a variety of spatiotemporal analysis methods such as data distribution test and variance analysis. A selected element is analyzed by an Empirical Orthogonal Function (EOF) analytical method for the main spatiotemporal distribution patterns. The basic idea of the EOF is to decompose a spatiotemporal variation field into a time-independent spatial function and a time-dependent temporal function which are relatively independent. The result of the EOF shows that an element to be analyzed is determined by several main spatial distribution patterns, and each distribution pattern has the corresponding temporal variation respectively, resulting in different intensities of each spatial pattern at different time.

For the analysis of extreme events, the regression period of each sea area and the element value under a certain regression period of a certain element when reaching a certain intensity are computed by an extreme value statistical method and a generalized extreme value statistical method. The purpose of the study and analysis is to provide basic background information on the ocean and provide reference for navigation planning over the season.

2) Study of the Characteristics of the Temperature-Salinity Relation

The study of the characteristics of the temperature-salinity relation is mainly based on statistical analysis of the above-mentioned spatiotemporal distribution characteristics of marine elements, and a reanalysis data product and the historical observation profile data of temperature and salinity are used for analyzing the temperature and salinity correlation statistics at different time scales in each sea area. The characteristic curves of temperature and salinity at different time scales in each sea area are determined to provide a data base for salinity correction.

Step 2: on the basis of analysis of the spatiotemporal characteristics and study of the characteristics of the temperature-salinity relation, a statistical prediction model of marine environmental dynamic elements is established by a spatiotemporal empirical orthogonal function method. Based on a high-resolution marine reanalysis product for a sea area to be analyzed and forecasted, a spatiotemporal sample matrix of daily marine dynamic environmental elements over the years in a space to be analyzed is constructed. The method for constructing the spatiotemporal sample matrix is as follows: for a certain marine dynamic environmental element, the corresponding spatiotemporal sample matrix X of the daily marine dynamic environmental element over the years in the space to be analyzed is:

$$X = \begin{bmatrix} x_{1,1}^1 & \cdots & x_{n,1}^1 & \cdots & x_{N,1}^1 & \cdots & x_{1,t}^1 & \cdots & x_{n,t}^1 & \cdots & x_{N,t}^1 & \cdots & x_{1,T}^1 & \cdots & x_{n,T}^1 & \cdots & x_{N,T}^1 \\ \vdots & \ddots & \vdots & \ddots & \vdots & \ddots & \vdots & \ddots & \vdots & \ddots & \vdots & \ddots & \vdots & \ddots & \vdots & \ddots & \vdots \\ x_{1,1}^m & \cdots & x_{n,1}^m & \cdots & x_{N,1}^m & \cdots & x_{1,t}^m & \cdots & x_{n,t}^m & \cdots & x_{N,t}^m & \cdots & x_{1,T}^m & \cdots & x_{n,T}^m & \cdots & x_{N,T}^m \\ \vdots & \ddots & \vdots & \ddots & \vdots & \ddots & \vdots & \ddots & \vdots & \ddots & \vdots & \ddots & \vdots & \ddots & \vdots & \ddots & \vdots \\ x_{1,1}^M & \cdots & x_{n,1}^M & \cdots & x_{N,1}^M & \cdots & x_{1,t}^M & \cdots & x_{n,t}^M & \cdots & x_{N,t}^M & \cdots & x_{1,T}^M & \cdots & x_{n,T}^M & \cdots & x_{N,T}^M \end{bmatrix} \quad (1)$$

where X represents the spatiotemporal sample matrix of daily marine dynamic environment elements over the years, n represents the number of spatial grid points, t represents the number of time series, and m represents the number of annual samples.

For any spatiotemporal sample matrix X, of which the matrix dimension is M×(N×T), singular value decomposition is performed for the spatiotemporal sample matrix X, the eigenvalues of the matrix and the eigenvector corresponding to each eigenvalue are obtained, the total proportion of each eigenvalue is computed in turn, and the eigenvalues and eigenvectors are arranged in order. The eigenvectors at this time are the time series of a spatial mode, which contain both spatial information and temporal information, and such an eigenvector is called spatiotemporal base.

Since the eigenvalues and eigenvectors of a covariance matrix of the spatiotemporal sample matrix X are usually solved by the Jacobi iterative method, when the rank of the matrix is large, the Jacobi iterative method requires a large amount of computation. The number N×T of the spatiotemporal grid points is much larger than the number of period M, so it is necessary to perform spatiotemporal transformation to reduce the amount of computation. Obviously, $C = X \cdot X^T$ and $C^* = X^T \cdot X$ have the same non-zero eigenvalues, but different eigenvectors. Therefore, after the eigenvectors of the C* matrix are obtained through matrix transformation, the eigenvectors of the C matrix can be computed, and the product of $\widetilde{X}_i$ and its transposed matrix can be expressed as follows:

$$C^* = \frac{1}{n} X^T \times X \quad (2)$$

The eigenvector $V_{M \times M}$ is:

$$C^* \times V^* = V^* \times \Lambda \quad (3)$$

where Λ is a diagonal square matrix corresponding to the eigenvalues, as follows:

$$\Lambda = \begin{bmatrix} \lambda_1 & \cdots & 0 & \cdots & 0 \\ \vdots & \ddots & \vdots & \vdots & \vdots \\ 0 & \cdots & \lambda_m & \cdots & 0 \\ \vdots & \vdots & \vdots & \ddots & \vdots \\ 0 & \cdots & 0 & \cdots & \lambda_M \end{bmatrix} \quad (4)$$

where $\lambda_1 > \ldots > \lambda_m > \ldots \lambda_M$.
Any eigenvector $V_m$ is as follows:

$$V_m = \frac{1}{\sqrt{\lambda_m}} \tilde{X}_i \times V^* \quad (5)$$

where each column of eigenvector values has one non-zero eigenvalue in one-to-one correspondence therewith, and such an operation is called spatiotemporal empirical orthogonal decomposition. The eigenvectors obtained by the spatiotemporal empirical orthogonal decomposition are the time series of a spatial mode, which contain both spatial and temporal information, which we call a spatiotemporal base. Each spatiotemporal base represents the evolution of spatial patterns over time. Therefore, the spatiotemporal empirical orthogonal decomposition method extracts the main characteristics of the temporal variation of the spatial patterns based on historical data.

The corresponding principal components can be obtained by projecting spatiotemporal modes onto the matrix $\widetilde{X}_i$, as follows:

$$PC_{M \times (N \times T)} = V^T_{M \times (N \times T)} \times \widetilde{X}_{i,M \times (N \times T)} \quad (6)$$

The principal components are the spatiotemporal coefficients corresponding to each spatiotemporal eigenvector. The spatiotemporal coefficients $PC_{M \times (N \times T)}$ is a M×(N×T) dimensional matrix, each row of data in $PC_{M \times (N \times T)}$ is the space-time coefficient corresponding to each space-time mode, the space-time coefficient of the first space-time mode corresponds to the first row of the spatiotemporal coefficient $PC_{M \times (N \times T)}$, and so on.

Using the proposed spatiotemporal empirical orthogonal function decomposition method, the prediction problem of marine dynamic environmental elements in an area to be analyzed can be transformed from a time extrapolation problem to a problem of finding similar processes from historical time series variations. A set of spatiotemporal bases is established using the decomposition results of multiple spatiotemporal series, and spatiotemporal series are predicted by spatiotemporal observations and the spatiotemporal bases.

The spatiotemporal observation value $O_i$ is as follows:

$$O_i = [o_{1,t-l} \cdots o_{N,t-l} \cdots o_{1,t-l+i} \cdots o_{N,t-l+i} \cdots o_{1,t} \cdots o_{N,t}]^T \quad (7)$$

where $O_i$ represents the spatiotemporal observation, t represents the prediction start time, n represents the number of spatial grid points, and l represents the number of observations.

The spatiotemporal base $H_i$ is divided into two parts: one is a fitting spatiotemporal base $H_{i,f}$ with the same period as the spatiotemporal observation, and the other is a predicted spatiotemporal base $H_{i,p}$.

$$H_i = \begin{bmatrix} h^1_{1,t-l} & \cdots & h^1_{N,t-l} & \cdots & h^1_{1,t-l+j} & \cdots & h^1_{N,t-l+j} & \cdots & h^1_{1,t+p} & \cdots & h^1_{N,t+p} \\ \vdots & \ddots & \vdots & \ddots & \vdots & \ddots & \vdots & \ddots & \vdots & \ddots & \vdots \\ h^m_{1,t-l} & \cdots & h^m_{N,t-l} & \cdots & h^m_{1,t-l+j} & \cdots & h^m_{N,t-l+j} & \cdots & h^m_{1,t+p} & \cdots & h^m_{N,t+p} \\ \vdots & \ddots & \vdots & \ddots & \vdots & \ddots & \vdots & \ddots & \vdots & \ddots & \vdots \\ h^M_{1,t-l} & \cdots & h^M_{N,t-l} & \cdots & h^M_{1,t-l+j} & \cdots & h^M_{N,t-l+j} & \cdots & h^M_{1,t+p} & \cdots & h^M_{N,t+p} \end{bmatrix}^T \quad (8)$$

For the spatiotemporal base decomposed for a historical long time, a spatial time series matrix can be divided into two parts: a fitting spatial time series matrix $H_{i,f}$ with the same time as the observation data and a forecasted spatial time series matrix $H_{i,p}$ with the same time as the prediction.

$$H_{i,f} = \begin{bmatrix} h^1_{1,t-l} & \cdots & h^1_{N,t-l} & \cdots & h^1_{1,t-l+j} & \cdots & h^1_{N,t-l+j} & \cdots & h^1_{1,t} & \cdots & h^1_{N,t} \\ \vdots & \ddots & \vdots & \ddots & \vdots & \ddots & \vdots & \ddots & \vdots & \ddots & \vdots \\ h^m_{1,t-l} & \cdots & h^m_{N,t-l} & \cdots & h^m_{1,t-l+j} & \cdots & h^m_{N,t-l+j} & \cdots & h^m_{1,t} & \cdots & h^m_{N,t} \\ \vdots & \ddots & \vdots & \ddots & \vdots & \ddots & \vdots & \ddots & \vdots & \ddots & \vdots \\ h^M_{1,t-l} & \cdots & h^M_{N,t-l} & \cdots & h^M_{1,t-l+j} & \cdots & h^M_{N,t-l+j} & \cdots & h^M_{1,t} & \cdots & h^M_{N,t} \end{bmatrix}^T \quad (9)$$

$$H_{i,p} = \begin{bmatrix} h^1_{1,t+1} & \cdots & h^1_{N,t+1} & \cdots & h^1_{1,t+j} & \cdots & h^1_{N,t+j} & \cdots & h^1_{1,t+p} & \cdots & h^1_{N,t+p} \\ \vdots & \ddots & \vdots & \ddots & \vdots & \ddots & \vdots & \ddots & \vdots & \ddots & \vdots \\ h^m_{1,t+1} & \cdots & h^m_{N,t+1} & \cdots & h^m_{1,t+j} & \cdots & h^m_{N,t+j} & \cdots & h^m_{1,t+p} & \cdots & h^m_{N,t+p} \\ \vdots & \ddots & \vdots & \ddots & \vdots & \ddots & \vdots & \ddots & \vdots & \ddots & \vdots \\ h^M_{1,t+1} & \cdots & h^M_{N,t+1} & \cdots & h^M_{1,t+j} & \cdots & h^M_{N,t+j} & \cdots & h^M_{1,t+p} & \cdots & h^M_{N,t+p} \end{bmatrix}^T \quad (10)$$

where t represents the start time of prediction, N represents the number of spatial grid points, l represents the number of observations, p represents the number of timesteps of prediction, and M represents the number of spatiotemporal bases.

The eigenvectors of the spatiotemporal matrix are orthogonal to each other, that is, the spatiotemporal base is linearly independent. For linearly independent base functions, Least Square Estimation (LSE) is the optimal fitting method. The fitting coefficients and fitting spatiotemporal bases of the spatiotemporal observations are solved by the LSE method. The fitting coefficients are projections of spatiotemporal observations on each spatiotemporal base, describing the similarity between a set of observations and the spatiotemporal base:

$$O_i = H_{i,f} S_i \quad (11)$$

where S represents the fitting coefficients, as follows:

$$S_i = [S_{i,1} \ldots S_{i,m} \ldots S_{i,M}] \quad (12)$$

where m represents the m-th mode.

Each spatiotemporal base can be regarded as a description of the rule of variation of a spatiotemporal series. Therefore, when the rule of the spatiotemporal series in the fitting stage can be described by the spatiotemporal base, the variation in the spatiotemporal series in the prediction stage also conforms to the same rule. From this, future values of the spatiotemporal series are predicted by reconstructing the fitting coefficients and predicting the spatiotemporal base. Therefore, the spatiotemporal series is predicted using a spatiotemporal empirical orthogonal function prediction model which combines the spatiotemporal empirical orthogonal decomposition method and the least square method, and the prediction model is as follows:

$$Y_i = H_{i,p} \cdot S_i = [y_{i,1,t+1} \ \cdots \ y_{i,N,t+1} \ \cdots \ y_{i,1,t+j} \ \cdots \ y_{i,N,t+j} \ \cdots \ y_{i,1,t+p} \ \cdots \ y_{i,N,t+p}]^T \quad (13)$$

where Y represents the spatiotemporal prediction result, N represents the number of spatial grid points, t represents the start time of prediction, and p represents the number of timesteps of prediction.

Step 3: based on the observation data of sea surface temperature and salinity obtained by a marine transportation platform, a marine environment forecast field around the marine transportation platform is corrected by using a real-time analysis technology of a marine environment field to improve the prediction accuracy of the marine environment around the marine transportation platform.

A real-time analysis technology of the marine environment field around the marine transportation platform aims to establish a modular data assimilation system installed on the marine transportation platform. Compared with a shore-based modular data assimilation system, the real-time analysis system of the marine environment of the marine transportation platform is smaller and more flexible in data processing and implementation methods, and has a function of analyzing and predicting the marine environment field below the water surface. Moreover, due to the limited means of obtaining observation data and less real-time observation data during the navigation of the marine transportation platform, the real-time analysis technology of the marine environment of the marine transportation platform has a particularity. To realize the real-time analysis of the marine environment of the marine transportation platform, it is necessary to solve the following technical problems: construction of a marine environment background field, inversion of a three-dimensional temperature and salinity field, assimilation of the observation data of the offshore platform, and the like.

1) Construction of the Marine Environment Background Field

Figure 2:
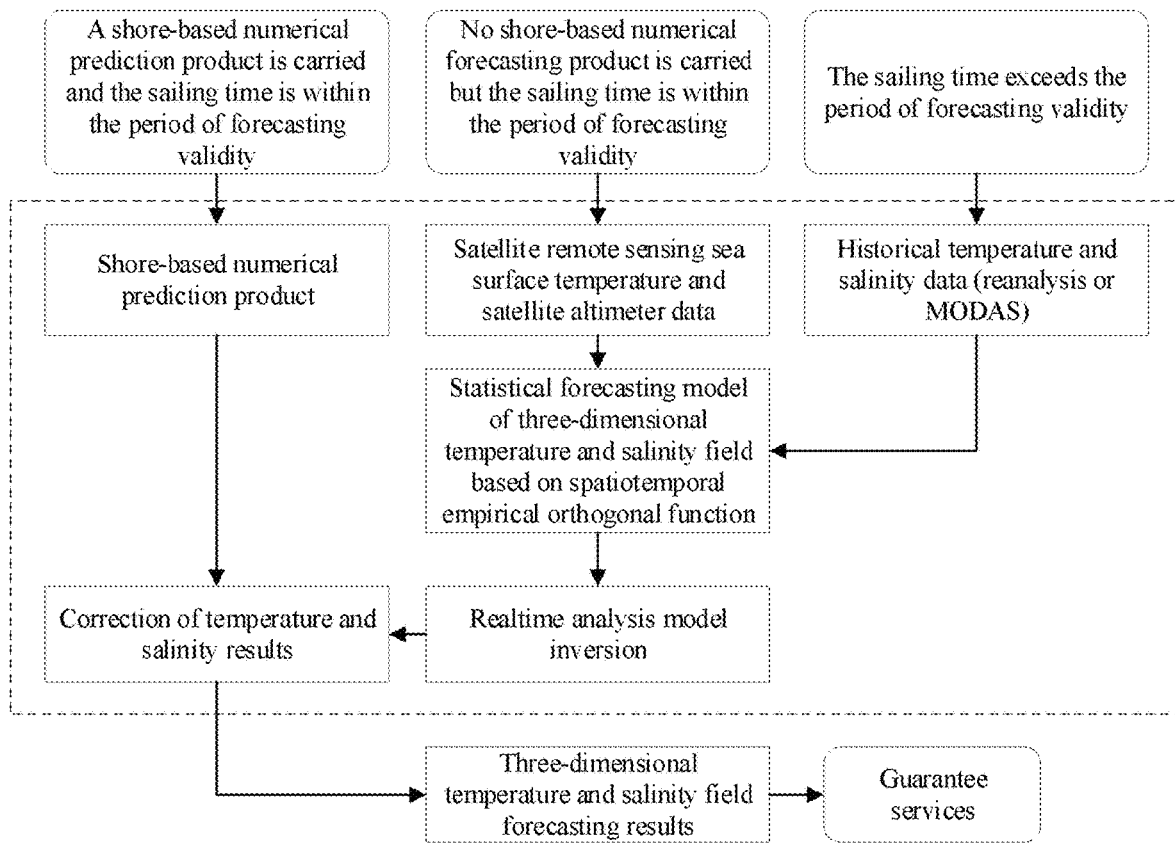
FIG. 2 shows selection modes of marine environment background fields in the method of the disclosure.

For the construction of the marine environment background field, combined with the characteristics of a marine transportation platform, the following three methods are proposed to obtain the marine environment background field according to available data, and the selection modes of different background fields are shown in FIG. 2.

a) When a shore-based marine numerical prediction product transmitted by a shore-based security department is available, the shore-based marine numerical prediction product is loaded into a marine environment database of the marine transportation platform before sailing, and used as the background field. Using a multi-scale marine data assimilation method, real-time/quasi-real-time multi-source marine observation data of the marine transportation platform is assimilated to form a high-precision real-time analysis field of the marine environment around the marine transportation platform.

b) When a shore-based numerical prediction product is not available, real-time/quasi-real-time satellite remote sensing sea surface temperature and satellite altimeter data published on the Internet can be directly downloaded, and loaded into a marine environment data platform of the marine transportation platform before sailing, and then underwater temperature and salinity data is inverted based on a real-time analysis system of the marine transportation platform. The three-dimensional temperature and salinity field obtained by the inversion can be used as an initial field for inertial prediction, which can provide the background field for real-time analysis of the marine environment in a short time before sailing, and make a real-time analysis product of the marine environment field around an underwater vehicle.

c) When the marine transportation platform has been sailing for a long time (more than 15 days) and the shore-based prediction product loaded fails, based on a reanalysis or statistical prediction product, underwater temperature and salinity data is inverted based on the real-time analysis system of the marine transportation platform, and a real-time analysis product of the marine environment field around the underwater vehicle is made.

2) Inversion of the Three-Dimensional Temperature and Salinity Field

Figure 3:
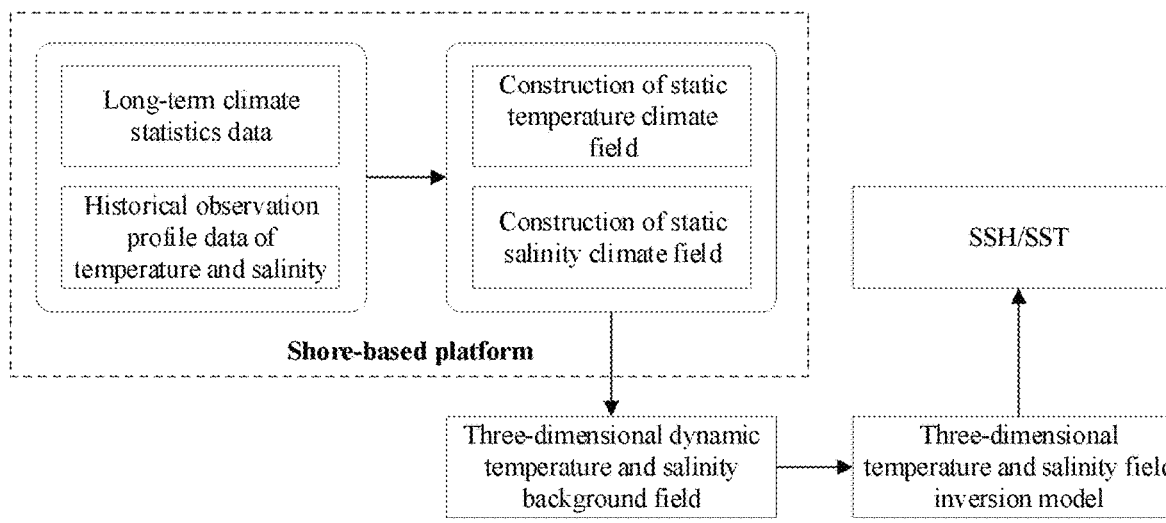
FIG. 3 shows a flow chart of inversion of a three-dimensional temperature and salinity field in the method of the disclosure.

Three-dimensional temperature and salinity field inversion is a main method to obtain a marine environmental field by using satellite remote sensing data to invert a three-dimensional temperature and salinity field when a shore-based prediction product and a real-time reanalysis data product are not available. Before sailing, the downloaded satellite sea surface temperature and sea surface height anomaly data are used for inverting to obtain the three-dimensional temperature and salinity field, and based on this, statistical prediction or inertial prediction of temperature and salinity is performed to construct a real-time analysis background field. The main technical processes include: construction of a static temperature and salinity climate field, construction of a dynamic background field, the inversion of the three-dimensional temperature and salinity field, and the like. An inversion process of the three-dimensional temperature and salinity field is shown in FIG. 3.

a) Construction of a Static Temperature Climate Field

Taking a temperature climatic state analysis product (such as WOA01) as an initial guess field, historical temperature profile observation data that has undergone processing and quality control is assimilated by using an optimal interpolation data assimilation technology, and static temperature climate field products at different water depths and each horizontal grid point are formed.

The temperature observation data $T_{j,k}^o$ at a position j is formed by the optimal interpolation method into the climatological temperature data $T_{i,k}^c$ at each grid point position i, at the k-th layer in depth:

$$T_{i,k}^c = T_{i,k}^B + \sum_{j=1}^{N} w_{i,j}\left(T_{j,k}^o - T_{j,k}^B\right) \tag{14}$$

where $T_{i,k}^B$ is the climatic background field (such as WOA01).

The weight coefficient $w_{i,j}$ in the above equation is solved by the following equation:

$$C_i W_i = F_i \tag{15}$$

where $w_{i,j}$ (j=1 ..., N) is an element of matrix $W_i$, and $c_{m,n}$ is an element of matrix $C_i$, which is equal to the sum of error covariance $c_{m,n}^{fg}$ of the initial guess temperature and covariance $c_{m,n}^o$ of observation errors $r_m$ and $r_n$ at different observation positions.

b) Construction of a Static Salinity Climate Field

Using historical observation data of temperature and salinity profiles that has undergone strict quality control and fine processing, for different regions, grids and different time periods, an empirical regression model of inversion of salinity from temperature is established using a regression analysis method.

$$S_{i,k}(T) = \overline{S_{i,k}} + a_{i,k}^{S1}(T - \overline{T_{i,k}}) \tag{16}$$

where $$\overline{S_{i,k}} = \frac{\sum_{j=1}^{N^{TS}} b_{i,j} S_{j,k}^o}{\sum_{j=1}^{N^{TS}} b_{i,j}} \tag{17}$$

$$\overline{T_{i,k}} = \frac{\sum_{j=1}^{N^{TS}} b_{i,j} T_{j,k}^o}{\sum_{j=1}^{N^{TS}} b_{i,j}} \tag{18}$$

$$a_{i,k}^{S1} = \frac{\sum_{j=1}^{N^{TS}} b_{i,j}\left(S_{j,k}^o - \overline{S_{j,k}}\right)\left(T_{j,k}^o - \overline{T_{j,k}}\right)}{\sum_{j=1}^{N^{TS}} b_{i,j}\left(T_{j,k}^o - \overline{T_{j,k}}\right)^2} \tag{19}$$

where $b_{i,j}$ is a local correlation function:

$$b_{i,j} = \exp\{-[(x_i - x_j)/L_x]^2 - [(y_i - y_j)/L_y]^2 - [(t_i - t_j)/L_t]^2\} \tag{20}$$

where x and y are the longitudinal and latitudinal positions respectively; t is time; $L_x$, $L_y$, and $L_t$ are length and time correlation scales respectively.

The static temperature climate field is substituted into the temperature-salinity correlation model established above to generate static salinity climate field products at different water depths and each horizontal grid point.

c) Inversion of a Temperature Profile From SST

On the basis of a lot of rigorous analysis of historical temperature observation data, an empirical regression model for the inversion of the temperature profile from SST is established:

$$T_{i,k}(SST) = \overline{T_{i,k}} + a_{i,k}^{T1}(sst - \overline{T_{i,1}}) \quad (21)$$

where $T_{i,k}$ (SST) is the temperature value at grid point i and depth k inverted from the sea surface temperature, $\overline{T_{i,k}}$ is the average temperature, SST is the sea surface temperature, and $a_{i,k}^{T1}$ is a regression coefficient.

d) Inversion of a Temperature Profile From SSH

On the basis of a lot of rigorous analysis of historical observation data of temperature and salinity, an empirical regression model for the inversion of the temperature profile from SSH is established:

$$T_{i,k}(h) = \overline{T_{i,k}} + a_{i,k}^{T2}(h - \overline{h_i}) \quad (22)$$

where $T_{i,k}(h)$ is the temperature value at grid point i and depth k inverted from sea surface height, $a_{i,k}^{T2}$ is a regression coefficient, and h and $\overline{h_i}$ are dynamic height anomaly (deviation) and its average value respectively.

The dynamic height anomaly (deviation) is computed by:

$$h = \int_0^H \frac{[v(T, S, p), -v(0, 35, p)]}{v(0, 35, p)} dz \quad (23)$$

where v is the specific volume of seawater, v(0,35, p) is the specific volume of seawater when the seawater temperature is 0° C. and the salinity is 35 psu, and H is the water depth.

In order to use as much temperature and salinity profile data as possible for regression analysis, it is necessary to use historical observation data of temperature and salinity profiles that has undergone strict quality control. For the observation data of temperature and salinity that does not reach the seabed depth, through repeated experiments, a temperature profile extension model is established based on an empirical orthogonal function analysis (EOF) method. The temperature observation data that does not reach the required depth is extended using the model to the seabed to obtain the entire temperature salinity profile. For the profile with missing salinity measurement, the salinity profile is obtained from the temperature profile by using the temperature-salinity relation model established above.

A complete temperature profile is obtained by superimposing a synthetic temperature profile $T_k^{syn}$ onto an observed profile with observation not reaching the seabed:

$$T_k = T_k^{syn} + [T_{k\,max}^o - T_{k\,max}^{syn}] \exp[-(z_k - z_{k\,max})/L_z] \quad (24)$$

where $L_z$ is a vertical correlation scale, $z_k > z_{k\,max}$.

The synthetic temperature profile $T_k^{syn}$ is computed by fitting the temperature profile observation that does not reach the seabed to the average temperature and superimposing the empirical orthogonal function $E_k$ corresponding to the maximum eigenvalue:

$$T_{j,k}^{syn} = \overline{T_{j,k}} + g_j e_k \quad (25)$$

where $g_j$ is the amplitude of the maximum orthogonal function, computed by:

$$g_j = \frac{\sum_{k=1}^{M_j} w_k [e_k(T_{j,k}^o - \overline{T_{j,k}})]}{\sum_{k=1}^{M_j} w_k} \quad (26)$$

where weight w is defined as $w_k = (z_k - z_{k-1})^{1/4}, k=2, \ldots, M_j$, $w_1 = w_2$.

e) Joint Inversion of a Temperature Profile From SST and SSH

On the basis of a lot of rigorous analysis of historical observation data of temperature and salinity, an empirical regression model for the inversion of the temperature profile from SST and SSH is established:

$$T_{i,k}(sst,h) = \overline{T_{i,k}} a_{i,k}^{T3}(SST - \overline{T_{i,1}}) + a_{i,k}^{T4}(h - \overline{h_i}) + a_{i,k}^{T5}[(SST - \overline{T_{i,1}})(h - \overline{h_i}) - \overline{hSST_i}] \quad (27)$$

where $T_{ik}$ (sst, h) is the temperature value at grid point i and depth k inverted by sea surface temperature and sea surface height anomalies (deviations), and $a_{i,k}^{T3}$, $a_{i,k}^{T4}$ and $a_{i,k}^{T5}$ are regression coefficients.

3) Assimilation of Observation Data of the Marine Transportation Platform

To improve the accuracy of real-time analysis as much as possible, the dynamic background field of the marine environment is further corrected by using the real-time observation data of temperature and salinity obtained by the marine transportation platform. The disclosure uses a multi-grid three-dimensional variational assimilation technology for correcting the background field. The method can quickly extract multi-scale information from an observation system from long wave to short wave in turn, occupies small memory, has high computing speed, and is very suitable for a computer carried on the marine transportation platform. In multigrid three-dimensional variational data assimilation, long-wave information can be analyzed using a coarse-grid objective functional, while short-wave information can be analyzed using a fine-grid objective functional. Therefore, the target functional in the multigrid three-dimensional variational data assimilation method is as follows:

$$J^{(n)} = \frac{1}{2} X^{(n)T} X^{(n)} + \frac{1}{2} (H^{(n)} X^{(n)} - Y^{(n)})^T O^{(n)-1} (H^{(n)} X^{(n)} - Y^{(n)}) \quad (28)$$

where $$\begin{cases} X = X^a - X^b \\ Y = Y^{obs} - HX^b \end{cases} \quad (29)$$

where n represents the n-th grid, n=1,2,3, ..., N, $X^b$ is a model background field (prediction field) vector, $X^a$ is an analysis field vector, $Y^{obs}$ is an observation field vector; O is an observation field error covariance matrix; H is a bilinear interpolation operator from the model grid to the observation point; X is a control variable, which represents the correction vector relative to the model background field vector, Y is the difference between the observation field and the model background field, and $$\begin{cases} Y^{(1)} = Y^{obs} - HX^b \\ Y^{(n)} = Y^{(n-1)} - H^{(n-1)}X^{(n-1)} (n = 2, 3, \ldots, N) \end{cases} \quad (30)$$

where coarse grids correspond to long-wave modes, and fine grids correspond to short-wave modes. Since the wavelength or correlation scale is expressed by the thickness of a grid, the background field error covariance matrix degenerates into a simple identity matrix. The final analysis result can be expressed as:

$$X^a = X^b + X_L = X^b + \sum_{n=1}^{N} X^{(n)} \quad (31)$$

From coarse grids to fine grids, three-dimensional variational analysis is performed on the increment of the observation field relative to the background field in turn. In the process of each analysis, the analysis field obtained from the previous analysis on a coarser grid is substituted into the analysis of a next finer grid as a new background field. The increment of each analysis also refers to the increment relative to the new background field obtained by the previous coarser grid analysis. Finally, the analysis results of all grids are superimposed to obtain the final analysis result. In the above multigrid three-dimensional variational method, the vertical gradient of marine environmental elements is proposed to be introduced into the objective functional as a constraint condition, so as to improve the analysis ability of a spring layer.

Step 4: The influence of salinity variation on density is non-negligible, and making statistical prediction for temperature and salinity separately will cause the destruction of the thermodynamic structure of a marine state field, which leads to dynamic instability of the ocean. To maintain the consistency of a sea surface temperature and salinity structure, correcting the salinity after the temperature and salinity are forecasted.

At present, there are many salinity adjustment schemes in the world. The European Centre for Medium-Range Weather Forecasts (ECMWF) adjusts the salinity by changing the temperature and salinity profiles. The NCEP in the United States adjusts the temperature and salinity using the observation data of sea surface height and temperature by the three-dimensional variational method. Learning from the salinity adjustment scheme of the ECMWF, in the disclosure, after the temperature and salinity are statistically forecasted, the salinity is adjusted by using a temperature-salinity relation curve, and the temperature-salinity relation is kept as close as possible to its climatic characteristics.

The disclosure uses the aforementioned statistical results to analyze the climatic seasonal characteristics of the temperature-salinity relation in each sea area, and simultaneously analyze the influence of high-frequency fluctuations of temperature and salinity on the temperature-salinity relation, thereby determining the temperature-salinity relation curves and envelopes of characteristics thereof in different sea areas and different seasons. The salinity data of which the prediction results deviate from the temperature-salinity curve is corrected by the nudging method.

What is claimed is:

1. A marine transportation platform guarantee-oriented analysis and prediction method for a three-dimensional temperature and salinity field, comprising:

(1) based on multi-source marine environmental data, analyzing spatiotemporal distribution characteristics of marine dynamic environmental elements, and studying characteristics of a temperature-salinity relation;
(2) based on analysis of the spatiotemporal characteristics and the study of the characteristics of the temperature-salinity relation, establishing a statistical prediction model of marine environmental dynamic elements by a spatiotemporal empirical orthogonal function method;
(3) based on observation data of sea surface temperature (SST) and salinity obtained by a marine transportation platform, correcting a marine environment forecast field around the marine transportation platform to improve prediction accuracy of a marine environment around the marine transportation platform; and
(4) navigating the marine transportation platform based on the marine environment forecast field;

wherein correcting the marine environment forecast field comprises:
obtaining the marine environment background field according to available data by:
a) when a shore-based marine numerical prediction product transmitted by a shore-based security department is available, loading the shore-based marine numerical prediction product into a marine environment database of the marine transportation platform before sailing, and, using the shore-based marine numerical prediction product as the background field, assimilating real-time/quasi-real-time multi-source marine observation data of the marine transportation platform by using a multi-scale marine data assimilation method to form a real-time analysis field of the marine environment around the marine transportation platform;
b) when the shore-based numerical prediction product is not available, downloading real-time/quasi-real-time satellite remote sensing sea surface temperature and satellite altimeter data, loading the real-time/quasi-real-time satellite remote sensing sea surface temperature and satellite altimeter data into a marine environment data platform of the marine transportation platform before sailing, inverting underwater temperature and salinity data based on a real-time analysis system of the marine transportation platform, thereby obtaining the three-dimensional temperature and salinity field, and using the three-dimensional temperature and salinity field as an initial field for inertial prediction;
c) when the marine transportation platform has been sailing for more than 15 days, and loading the shore-based prediction product fails, based on a reanalysis or statistical prediction product, inverting underwater temperature and salinity data based on the real-time analysis system of the marine transportation platform, and making a real-time analysis product of the marine environment field around the underwater vehicle;

wherein inversion of the three-dimensional temperature and salinity field comprises:
a) construction of a static temperature climate field by:
taking a temperature climatic state analysis product as an initial guess field, historical temperature profile observation data that has undergone processing and quality control is assimilated by using an interpolation data assimilation technique to form static temperature climate field products at different water depths and each of a plurality of horizontal grid points;

temperature observation data $T_{j,k}^o$ at a position j is formed by an interpolation method into climatological temperature data $T_{i,k}^c$ at each grid point position i, at the k-th layer in depth:

$$T_{i,k}^c = T_{i,k}^B + \sum_{j=1}^{N} w_{i,j}(T_{j,k}^o - T_{j,k}^B) \quad (1)$$

where $T_{i,k}^B$ is the climatic background field;
weight coefficient $w_{i,j}$ in equation (1) is solved by equation (2):

$$C_i W_i = F_i \quad (2)$$

where $W_{i,j}^{(j=1,\ldots,N)}$ is an element of matrix $W_i$, and $C_{m,n}$ is an element of matrix $C_i$, which is equal to a sum of error covariance $C_{m,n}^{fs}$ of an initial guess temperature and covariance $c_{m,n}^o$ of observation errors $r_m$ and $r_n$ at different observation positions;

b) construction of a static salinity climate field by:

using historical observation data of temperature and salinity profiles for different regions, grids, and different time periods, an empirical regression model of inversion of salinity from temperature is established by using a regression analysis method:

$$S_{i,k}(T) = \overline{S_{i,k}} + a_{i,k}^{S1}(T - \overline{T_{i,k}}) \quad (3)$$

where $$\overline{S_{i,k}} = \frac{\sum_{j=1}^{N^{TS}} b_{i,j} S_{j,k}^O}{\sum_{j=1}^{N^{TS}} b_{i,j}} \quad (4)$$

$$\overline{T_{i,k}} = \frac{\sum_{j=1}^{N^{TS}} b_{i,j} T_{j,k}^O}{\sum_{j=1}^{N^{TS}} b_{i,j}} \quad (5)$$

$$a_{i,k}^{S1} = \frac{\sum_{j=1}^{N^{TS}} b_{i,j}(S_{j,k}^O - \overline{S_{j,k}})(T_{j,k}^O - \overline{T_{j,k}})}{\sum_{j=1}^{N^{TS}} b_{i,j}(T_{j,k}^O - \overline{T_{j,k}})^2} \quad (6)$$

where $b_{i,j}$ is a local correlation function:

$$b_{i,j} = \exp\{-[(x_i - x_j)/L_x]^2 - [(y_i - y_j)/L_y]^2 - [(t_i - t_j)/L_t]^2\} \quad (7)$$

where x and y are longitudinal and latitudinal positions respectively; t is time; $L_x$, $L_y$, and $L_t$ are length and time correlation scales respectively;

the static temperature climate field is substituted into a temperature-salinity correlation model established above to generate static salinity climate field products at different water depths and each horizontal grid point;

c) inversion of a temperature profile from the SST by:

on the basis of analysis of historical temperature observation data, an empirical regression model for the inversion of the temperature profile from SST is established:

$$T_{i,k}(SST) = \overline{T_{i,k}} + a_{i,k}^{T1}(sst - \overline{T_{i,1}}) \quad (8)$$

where $T_{i,k}(SST)$ is the temperature value at grid point i and depth k inverted from the sea surface temperature, $\overline{T_{i,k}}$ is the average temperature, SST is the sea surface temperature, and $a_{i,k}^{T1}$ a regression coefficient;

d) inversion of a temperature profile from sea surface height (SSH) by:

on the basis of analysis of historical observation data of temperature and salinity, an empirical regression model for the inversion of the temperature profile from SSH is established:

$$T_{i,k}(h) = \overline{T_{i,k}} + a_{i,k}^{T2}(h - \overline{h_i}) \quad (9)$$

where $T_{i,k}(h)$ is the temperature value at grid point i and depth k inverted from sea surface height, $a_{i,k}^{T2}$ sear is a regression coefficient, and h and $\overline{h_i}$ are dynamic height anomaly (deviation) and its average value respectively; the dynamic height anomaly is computed by:

$$h = \int_0^H \frac{[v(T, S, p) - v(0, 35, p)]}{v(0, 35, p)} dz \quad (10)$$

where v is the specific volume of seawater, v (0,35, p) is the specific volume of seawater when the seawater temperature is 0° C. and the salinity is 35 psu, and H is the water depth;

a temperature profile extension model is established based on an empirical orthogonal function analysis method; for a profile with missing salinity measurement, the salinity profile is obtained from the temperature profile by using the temperature-salinity relation model established above;

a complete temperature profile is obtained by superimposing a synthetic temperature profile $T_k^{syn}$ onto an observed profile with observation not reaching the seabed:

$$T_k = T_k^{syn} + [T_{k\,max}^o - T_{k\,max}^{syn}] \exp[-(z_k - z_{k\,max})/L_z] \quad (11)$$

where $L_z$ is a vertical correlation scale, $z_k > Z_{kmax}$;

the synthetic temperature profile $T_k^{syn}$ is computed by fitting the temperature profile observation that does not reach the seabed to the average temperature and superimposing the empirical orthogonal function $E_k$ corresponding to the maximum eigenvalue:

$$T_{j,k}^{syn} = \overline{T_{j,k}} + g_j e_k \quad (12)$$

where $g_j$ is the amplitude of the maximum orthogonal function, computed by:

$$g_j = \frac{\sum_{k=1}^{M_j} w_k [e_k(T_{j,k}^o - \overline{T_{j,k}})]}{\sum_{k=1}^{M_j} w_k} \quad (13)$$

where weight w is defined as $W_k = (Z_k - Z_{k-1})^{1/4}$, k=2, ..., $M_j$, $W_1 = w_2$; and e) joint inversion of a temperature profile from SST and SSH by:
  on the basis of analysis of historical observation data of temperature and salinity, an empirical regression model for the inversion of the temperature profile from SST and SSH is established:

$$T_{i,k}(sst,h)=\overline{T_{i,k}}+a_{i,k}^{T3}(SST-\overline{T_{i,t}})+a_{i,k}^{T4}(h-\overline{h_i})+a_{i,k}^{T5}[(SST-\overline{T_{i,1}})(h-\overline{h_i})-\overline{hSST_i}] \quad (14)$$

where $T_{i,k}$ (sst,h) is the temperature value at grid point i and depth k inverted by sea surface temperature and sea surface height anomalies (deviations), and $\alpha_{i,k}^{T3}$, $\alpha_{i,k}^{T4}$ and $\alpha_{i,k}^{T5}$ are regression coefficients;

wherein correcting the marine environment forecast field by assimilation of observation data of the marine transportation platform comprises:
correcting the background field by a multi-grid three-dimensional variational assimilation technique comprising:

$$J^{(n)}=\tfrac{1}{2}X^{(n)T}X^{(n)}+\tfrac{1}{2}(H^{(n)}X^{(n)}-Y^{(n)})^T O^{(n)-1}(H^{(n)}X^{(n)}-Y^{(n)}) \quad (15)$$

where $$\begin{cases} X = X^a - X^b \\ Y = Y^{obs} - HX^b \end{cases} \quad (16)$$

where n represents the n-th grid, n=1, 2,3, . . . , N, $X^b$ is a model background field (prediction field) vector, $X^a$ is an analysis field vector, $Y^{obs}$ is an observation field vector; O is an observation field error covariance matrix; H is a bilinear interpolation operator from the model grid to the observation point; X is a control variable, which represents the correction vector relative to the model background field vector, Y is the difference between the observation field and the model background field, and $$\begin{cases} Y^{(1)} = Y^{obs} - HX^b \\ Y^{(n)} = Y^{(n-1)} - H^{(n-1)}X^{(n-1)} (n = 2, 3, \ldots, N) \end{cases} \quad (17)$$

where coarse grids correspond to long-wave modes, and fine grids correspond to short-wave modes; and since the wavelength or correlation scale is expressed by the thickness of the grid, the background field error covariance matrix degenerates into an identity matrix:

$$X^a = X^b + X_L = X^b + \sum_{n=1}^{N} X^{(n)}; \quad (18)$$

and further comprising adjusting the salinity using a temperature-salinity relation curve after the temperature and salinity are forecasted, so as to keep the temperature-salinity relation matched to climatic characteristics.

2. The marine transportation platform guarantee-oriented analysis and prediction method for a three-dimensional temperature and salinity field according to claim 1, wherein constructing the spatiotemporal sample matrix in the step (2) comprises:
  for a certain marine dynamic environmental element, the corresponding spatiotemporal sample matrix X of daily marine dynamic environmental element over the years in the space to be analyzed is:

$$X = \begin{bmatrix} x_{1,1}^1 & \cdots & x_{n,1}^1 & \cdots & x_{N,1}^1 & \cdots & x_{1,t}^1 & \cdots & x_{n,t}^1 & \cdots & x_{N,t}^1 & \cdots & x_{1,T}^1 & \cdots & x_{n,T}^1 & \cdots & x_{N,T}^1 \\ \vdots & \ddots & \vdots & \ddots & \vdots & \vdots & \vdots & \ddots & \vdots & \ddots & \vdots & \vdots & \vdots & \ddots & \vdots & \ddots & \vdots \\ x_{1,1}^m & \cdots & x_{n,1}^m & \cdots & x_{N,1}^m & \cdots & x_{1,t}^m & \cdots & x_{n,t}^m & \cdots & x_{N,t}^m & \cdots & x_{1,T}^m & \cdots & x_{n,T}^m & \cdots & x_{N,T}^m \\ \vdots & \ddots & \vdots & \ddots & \vdots & \vdots & \vdots & \ddots & \vdots & \ddots & \vdots & \vdots & \vdots & \ddots & \vdots & \ddots & \vdots \\ x_{1,1}^M & \cdots & x_{n,1}^M & \cdots & x_{N,1}^M & \cdots & x_{1,t}^M & \cdots & x_{n,t}^M & \cdots & x_{N,t}^M & \cdots & x_{1,T}^M & \cdots & x_{n,T}^M & \cdots & x_{N,T}^M \end{bmatrix} \quad (19)$$

where X represents the spatiotemporal sample matrix of daily marine dynamic environment elements over the years, n represents the number of spatial grid points, t represents the number of time series, and m represents the number of annual samples;

for any spatiotemporal sample matrix X, of which the matrix dimension is M×(N×T), singular value decomposition is performed for the spatiotemporal sample matrix X, the eigenvalues of the matrix and the eigenvector corresponding to each eigenvalue are obtained, the total proportion of each eigenvalue is computed in turn, and the eigenvalues and eigenvectors are arranged in order; the eigenvectors at this time are the time series of a spatial mode, which comprise both spatial information and temporal information, and such an eigenvector is called a spatiotemporal base;

after the eigenvectors of the C* matrix are obtained through matrix transformation, the eigenvectors of the C matrix are computed, and the product of X and its transposed matrix is expressed as follows:

$$C^* = \frac{1}{n} X^T \times X \quad (20)$$

the eigenvector $V_{M \times M}$ IS:

$$C^* \times V^* = V^* \times \Lambda \quad (21)$$

where $\Lambda$ is a diagonal square matrix corresponding to the eigenvalues, as follows:

$$\Lambda = \begin{bmatrix} \lambda_1 & \cdots & 0 & \cdots & 0 \\ \vdots & \ddots & \vdots & \vdots & \vdots \\ 0 & \cdots & \lambda_m & \cdots & 0 \\ \vdots & \vdots & \vdots & \ddots & \vdots \\ 0 & \cdots & 0 & \cdots & \lambda_M \end{bmatrix} \quad (22)$$

where $\lambda_1 > \ldots \mu_m > \ldots \lambda_{>M}$, and $\lambda \geq 0$;

any eigenvector $V_m$ is as follows:

$$V_m = \frac{1}{\sqrt{\lambda_m}} \widetilde{X}_i \times V^* \qquad (23)$$

where each column of eigenvector values has one non-zero eigenvalue in one-to-one correspondence therewith, and such an operation is called spatiotemporal empirical orthogonal decomposition; the eigenvectors obtained by the spatiotemporal empirical orthogonal decomposition are the time series of the spatial mode, which contain both spatial and temporal information, which we call a spatiotemporal base; each spatiotemporal base represents the evolution of spatial patterns over time; therefore, the spatiotemporal empirical orthogonal decomposition method extracts the main characteristics of the temporal variation of the spatial patterns based on historical data;

the corresponding principal components are obtained by projecting spatiotemporal modes onto the matrix X, as follows:

$$PC_{M\times(N\times T)} = V^T_{M\times(N\times T)} \times X_{M\times(N\times T)} \qquad (24)$$

the principal components are the spatiotemporal coefficients corresponding to each spatiotemporal eigenvector; all row vectors in the spatiotemporal coefficients correspond to the principal components of the eigenvectors, the first row PC (1,:) is the principal component of the first spatiotemporal mode;

a set of spatiotemporal bases is established using the decomposition results of multiple spatiotemporal series, and spatiotemporal series are predicted by spatiotemporal observations and the spatiotemporal bases;

the spatiotemporal observation value $O_i$ is as follows:

$$O_i = [o_{1,t-l} \cdots o_{N,t-l} \cdots o_{1,t-l+i} \cdots o_{N,t-l+i} \cdots o_{1,t} \cdots o_{N,t}]^T \qquad (25)$$

where $O_i$ represents the spatiotemporal observation, t represents the prediction start time, n represents the number of spatial grid points, and I represents the number of observations;

the spatiotemporal base $H_i$ is divided into two parts: one is a fitting spatiotemporal base $H_{i,f}$ with the same period as the spatiotemporal observation, and the other is a predicted spatiotemporal base $H_{i,p}$;

$$H_i = \begin{bmatrix} h^1_{1,t-l} & \cdots & h^1_{N,t-l} & \cdots & h^1_{1,t-l+j} & \cdots & h^1_{N,t-l+j} & \cdots & h^1_{1,t+p} & \cdots & h^1_{N,t+p} \\ \vdots & \ddots & \vdots & \ddots & \vdots & \ddots & \vdots & \ddots & \vdots & \ddots & \vdots \\ h^m_{1,t-l} & \cdots & h^m_{N,t-l} & \cdots & h^m_{1,t-l+j} & \cdots & h^m_{N,t-l+j} & \cdots & h^m_{1,t+p} & \cdots & h^m_{N,t+p} \\ \vdots & \ddots & \vdots & \ddots & \vdots & \ddots & \vdots & \ddots & \vdots & \ddots & \vdots \\ h^M_{1,t-l} & \cdots & h^M_{N,t-l} & \cdots & h^M_{1,t-l+j} & \cdots & h^M_{N,t-l+j} & \cdots & h^M_{1,t+p} & \cdots & h^M_{N,t+p} \end{bmatrix}^T \qquad (26)$$

for the spatiotemporal base decomposed for a historical time, a spatial time series matrix are divided into two parts: a fitting spatial time series matrix $H_{i,f}$ with the same time as the observation data and a forecasted spatial time series matrix $H_{i,p}$ with the same time as the prediction;

$$H_{i,f} = \begin{bmatrix} h^1_{1,t-l} & \cdots & h^1_{N,t-l} & \cdots & h^1_{1,t-l+j} & \cdots & h^1_{N,t-l+j} & \cdots & h^1_{1,t} & \cdots & h^1_{N,t} \\ \vdots & \ddots & \vdots & \ddots & \vdots & \ddots & \vdots & \ddots & \vdots & \ddots & \vdots \\ h^m_{1,t-l} & \cdots & h^m_{N,t-l} & \cdots & h^m_{1,t-l+j} & \cdots & h^m_{N,t-l+j} & \cdots & h^m_{1,t} & \cdots & h^m_{N,t} \\ \vdots & \ddots & \vdots & \ddots & \vdots & \ddots & \vdots & \ddots & \vdots & \ddots & \vdots \\ h^M_{1,t-l} & \cdots & h^M_{N,t-l} & \cdots & h^M_{1,t-l+j} & \cdots & h^M_{N,t-l+j} & \cdots & h^M_{1,t} & \cdots & h^M_{N,t} \end{bmatrix}^T \qquad (27)$$

$$H_{i,p} = \begin{bmatrix} h^1_{1,t+1} & \cdots & h^1_{N,t+1} & \cdots & h^1_{1,t+j} & \cdots & h^1_{N,t+j} & \cdots & h^1_{1,t+p} & \cdots & h^1_{N,t+p} \\ \vdots & \ddots & \vdots & \ddots & \vdots & \ddots & \vdots & \ddots & \vdots & \ddots & \vdots \\ h^m_{1,t+1} & \cdots & h^m_{N,t+1} & \cdots & h^m_{1,t+j} & \cdots & h^m_{N,t+j} & \cdots & h^m_{1,t+p} & \cdots & h^m_{N,t+p} \\ \vdots & \ddots & \vdots & \ddots & \vdots & \ddots & \vdots & \ddots & \vdots & \ddots & \vdots \\ h^M_{1,t+1} & \cdots & h^M_{N,t+1} & \cdots & h^M_{1,t+j} & \cdots & h^M_{N,t+j} & \cdots & h^M_{1,t+p} & \cdots & h^M_{N,t+p} \end{bmatrix}^T \qquad (28)$$

where t represents the start time of prediction, N represents the number of spatial grid points, l represents the number of observations, p represents the number of timesteps of prediction, and M represents the number of spatiotemporal bases;

the eigenvectors of the spatiotemporal matrix are orthogonal to each other, such that the spatiotemporal base is linearly independent; the fitting coefficients and fitting spatiotemporal bases of the spatiotemporal observations are solved by a least squares estimation method; the fitting coefficients are projections of spatiotemporal observations on each spatiotemporal base, describing the similarity between a set of observations and the spatiotemporal base:

$$O_i = H_{i,l} S_i \tag{29}$$

where S represents the fitting coefficients, as follows:

$$S_i = [S_{i,1} \ldots S_{i,m} \ldots S_{i,M}] \tag{30}$$

where m represents the m-th mode;

the spatiotemporal series is predicted using a spatiotemporal empirical orthogonal function prediction model which combines the spatiotemporal empirical orthogonal decomposition method and the least squares method, and the prediction model is as follows:

$$Y_i = H_{i,p} \cdot S_i = \tag{31}$$

$$[y_{i,1,t+1} \ldots y_{i,N,t+1} \ldots y_{i,1,t+j} \ldots y_{i,N,t+j} \ldots y_{i,1,t+p} \ldots y_{i,N,t+p}]^T$$

where Y represents the spatiotemporal prediction result, N represents the number of spatial grid points, t represents the start time of prediction, and p represents the number of timesteps of prediction.

\* \* \* \* \*